United States Patent [19]

Grimminger et al.

[11] Patent Number: 5,219,662
[45] Date of Patent: Jun. 15, 1993

[54] BIOCOMPATIBLE POLYURETHANES BY TREATMENT WITH POLYOXAZOLINE BLOCK COPOLYMERS

[75] Inventors: Lisa C. Grimminger, Oxford; Sharon L. Haynie, Philadelphia, both of Pa.; Mureo Kaku, Wilmington, Del.; Dotsevi Y. Sogah, Ithaca, N.Y.

[73] Assignee: E. I. Du Pont de Nemours and Company, Wilmington, Del.

[21] Appl. No.: 704,762

[22] Filed: May 23, 1991

[51] Int. Cl.$^5$ .............................. B32B 27/40
[52] U.S. Cl. ............................. 428/423.1; 427/2; 523/105; 523/112
[58] Field of Search ............ 428/423.1, 423.5; 523/112, 105; 427/2

[56] References Cited

U.S. PATENT DOCUMENTS

| | | | |
|---|---|---|---|
| 3,300,274 | 1/1967 | Pittman et al. | 8/127.6 |
| 3,483,141 | 12/1969 | Litt et al. | 260/2 |
| 4,521,564 | 6/1985 | Solomon et al. | 525/54.1 |
| 4,786,556 | 11/1988 | Hu et al. | 428/423.5 |
| 4,841,007 | 6/1989 | Zdrahala et al. | 528/28 |

*Primary Examiner*—Paul J. Thibodeau
*Assistant Examiner*—D. S. Nakarani
*Attorney, Agent, or Firm*—Barbara C. Siegell

[57] ABSTRACT

Polyurethane surfaces are made more biocompatible, particularly with blood, by treatment with a block copolymer of a fluorinated oxazoline and either 2-methyl- or 2-ethyl-2-oxazoline. Such polyurethanes are useful as vascular graft or artificial heart parts.

33 Claims, No Drawings

BIOCOMPATIBLE POLYURETHANES BY TREATMENT WITH POLYOXAZOLINE BLOCK COPOLYMERS

BACKGROUND OF THE INVENTION

1. Field of the Invention

A polyurethane whose surface is treated with a block copolymer Of a 2-(2-perfluoroalkylethyl)-2-oxazoline and 2-methyl- or 2-ethyl-2-oxazoline has improved biocompatability and is suitable for use as a vascular graft.

Polyurethanes have relatively good biocompatability with blood and other body fluids, and have been used for artificial implants where there is blood contact, such as vascular grafts and artificial heart parts. However, as with all implants, any lack of biocompatibility is always a concern, and improvements are, of course, always desirable. The instant invention improves the biocompatability of polyurethane surfaces by treatment of the surfaces with selected polyoxazolines.

2. Technical Background

U.S. Pat. No. 3,483,141 reports the preparation of polymers of the containing the repeat unit

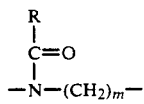

wherein m is 2 or 3 and R may be $CF_3(CX_2)_n-$, where n is an integer from 0 to 15 and X is hydrogen or halogen, especially chlorine or fluorine. The fluorine containing polymers are reported to be useful as water-and oil-repellent coatings for leather and fabric. There is no mention in this patent of treating polyurethanes or of biocompatability.

U.S. Pat. No. 3,300,274 discloses that polymers with the repeat units

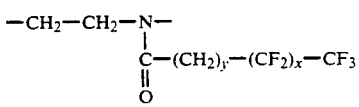

wherein y is 1 to 18 and x is 0 to 18. These polymers (and the aziridines from which they are made) are reported to be useful for treatment of (artificial and natural) fibers and textiles to enhance their oil and water repellency. There is no mention in this patent of treating polyurethanes or of biocompatability.

SUMMARY OF THE INVENTION

This invention concerns a process for manufacturing a polyurethane part, comprising, contacting the polyurethane's surface with an aqueous solution of a water soluble block copolymer of the structure

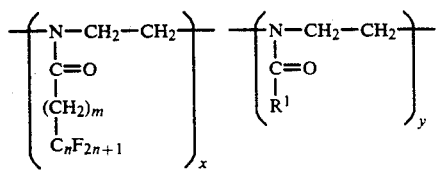

wherein:
m is 0, 1, or 2;
n is an integer of 4 to about 16;
x is an integer of 3 to 100;
y is large enough so that the polymer is water soluble; and
$R^1$ is methyl or ethyl.

This invention also concerns an article, comprising, a polyurethane part whose surface has been modified by contact with a block copolymer of the formula

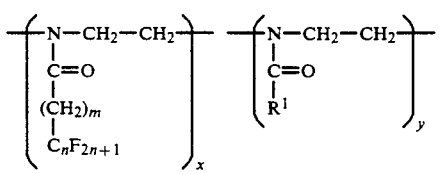

wherein
m is 1, 1, or 2;
n is an integer of 4 to about 16;
x is an integer of 3 to 100;
y is large enough so that the polymer is water soluble; and
$R^1$ is methyl or ethyl.

DETAILS OF THE INVENTION

In the following description of the details of the invention, the materials and conditions, and their preferred forms, apply to both processes and article herein.

Polyurethanes are polymers that are well known to those skilled in the art. For example, a good description of the technology and materials used in polyurethanes is found in G. Oertel, Ed., "Polyurethane Handbook", Hanser Publisher, Munich, 1985. Of especial interest are Chapters 2 and 3, which are hereby included by reference.

Polyurethanes may be rigid or flexible; the flexible type is preferred in the instant invention. Polyurethane polymers are generally made up of three ingredients, a high molecular weight polyol, an isocyanate, and a low molecular weight polyol and/or low molecular weight diamine (the latter are sometimes called polyurethane ureas, but fall within the definition of "polyurethane" herein). The high molecular weight polyol reacts with the isocyanate to form the so called soft segment, and the low molecular weight polyol (often a diol) and/or diamine, reacts to form the so-called hard segment.

Any high molecular weight polyol conventionally suitable for polyurethanes may be used, such as a polyester or a polyether. Polyethers are preferred high molecular weight polyols, and poly(tetramethylene ether) glycol is especially preferred. One or more diamines containing 2 to 6 carbon atoms are the preferred low molecular weight compounds, and a combination of ethylenediamine and cyclohexanediamine is especially preferred. Isocyanates useful include, but are not limited to toluenediisocyanate, isophorone diisocyanate, and bis(4-isocyanatophenyl)methane. Bis(4-isocyanatophenyl)methane is a preferred isocyanate. The polyurethanes can be made by conventional methods, and some are commercially available.

In the block copolymer it is preferred that n is 6 to 12 and more preferred that n is 8. It is preferred that $R^1$ is methyl, and that x is 4 to 8. It is also preferred that y is 6 or more. It is also preferred that m is 2.

It will be understood by those skilled in the art that the values for x and y are arithmetic averages for all of the individual polymer molecules in the block copolymer sample chosen. The art skilled realize that polymerizations that produce such block copolymers yield block copolymers wherein x or y has a statistical distribution over the total sample.

The minimum number of monomer units in the block copolymer derived from 2-ethyl- or 2-methyl-2-oxazoline is the number needed to make the block copolymer water soluble. This will vary, depending on n and x. Generally speaking the higher either or both of these are, the higher the number for y is required. In other words, the more fluorine in the fluoroalkyl substituted block, the higher the minimum number of monomer units needed in the unfluorinated block. The minimum size (number of monomer units, y) of the unfluorinated block needed for any given fluorine containing block is easily determined by a few simple solubility experiments with block copolymers of varying unfluorinated block size. In a particularly preferred polymer, x is 5, y is 9, m is 2, and n is 8.

In the process for the modification of the polyurethane surface, the concentration of the block copolymer is not critical, about 0.1 to about 20 weight percent, preferably about 0.5 to about 5 weight percent, being useful. The temperature is also not critical, ambient temperature being convenient. Similarly not critical is the contact time, a few hours normally being sufficient. It is preferred if the solution of the block copolymer is agitated or otherwise moved with respect to the polyurethane surface during the treatment.

The surface modified polyurethanes of the instant invention are useful as implants and parts where biocompatability, especially biocompatability with blood (hemocompatible) is important. Thus the surface modified polyurethaes have an improved resistance to formation of a thrombus on the surface. This makes these useful for vascular grafts, catheters, cannulas, extracorporeal oxygenators, heart assist devices, hemodialyzers, and parts for artificial hearts. It is particularly important that the polyurethane surfaces that contact blood be modified by the instant process.

The following Examples illustrate the improved biocompatability of polyurethane surfaces treated according to the instant invention. In these Examples the polymer tubing used was 4 mm inside diameter. Various types of polymers, including the polyurethane, were tested simultaneously in test loops. The polyurethane used was a copolymer of about one mole of polytetramethylene ether glycol having a molecular weight of about 1800, about 1.6 moles of bis(4-isocyanatophenyl)methane, and about 0.6 moles (total) of a 9:1 molar ratio of ethylene diamine and cyclohexanediamine, as described in U.S. Pat. No. 3,428,711. The tubing was made by spinning dimethylacetamide (DMAC) solutions of the polymer through an annular die. Typical wall thicknesses were 0.2–0.5 mm. For each of the Examples each sample of polymer tubing was washed with distilled, deionized water. The tubing was cut into 7-10 cm lengths, placed in a 15 mL polypropylene centrifuge tube which was filled with isotonic saline to cover the tube. The tubes were sterilized by various means, gamma irradiation being used for the polyurethane tubes.

The tubes were treated with the oxazoline block copolymer of Experiment 2 as follows. The tubing segments were connected with nylon (Example 1) or "Teflon" (Registered Trademark, E. I. du Pont de Nemours & Co., Inc.) (Example 2) connectors. A 1% (w/v) aqueous solution of the block copolymer was filtered through a 0.45 micron filter to remove particulates. Holding one end of the tubing up in the air, the other end was connected to a syringe, and the block copolymer solution was smoothly added to the tube in a manner to avoid any air bubbles on the side. The tubing was formed into an ellipse (the polyurethane sections were in the straighter part of the tube) and connected to a peristaltic pump. The copolymer solution was circulated for 30 min at 100 mL/min, and then allowed to stand overnight. Phosphate buffered saline solution was then pumped through the tubing (100 mL/min) for 1 min. Control samples of tubing were treated in the same way, except isotonic sterile saline solution was used instead of the block copolymer solution. The surfaces of the coated and uncoated polyurethane tubes were analyzed by X-ray photoelectron spectroscopy, and which showed the following surface analyses:

|  | % C | % F | % N |
| --- | --- | --- | --- |
| Coated | 53.2 | 31.3 | 3.9 |
| Uncoated | 75.5 | 0.3 | 2.1 |

This shows the presence of the oxazoline block copolymer on the surface of the polyurethane.

Experiment 1

2-Perfluorooctylethyl-2-oxazoline

Twenty g (42.2 mmol) of 3-perfluorooctylpropionitrile and 0.56 g (2.12 mmol, 5 mol% of nitrile) of $Cd(OAc)_2 \cdot 2H_2O$ were placed in a 100-ml three-necked flask which was equipped with a condenser connected to a water bath for trapping the $NH_3$ gas and a thermometer. The set-up was evacuated for 30 minutes and then vented with $N_2$. Twenty-one ml of nBuOH and 3.86 g (63.4 mmol) of ethanolamine were added under $N_2$, and the mixture was heated up to 130° C. for 48 hrs with stirring. The reaction was followed by GC-MASS. After the completion of reaction, n-BuOH was removed by distillation in vacuo (~78° C./23 mmHg). The crude product was obtained by distillation at 91.8°–92.6° C./1.2 mmHg in 60.8% yield. The distillation was repeated at least twice to obtain polymerization grade material $^1$H-NMR (QE-300, $CDCl_3$, δ ppm): 2.40–2.62 ($CF_2CH_2CH_2$,4H,m) 3.87 ($NCH_2$,2H,t), 4.30 ($CH_2O$, 2H, t). IR νC-F (1220 cm-1). Calculated for $C_{13}H_8F_{17}NO$ (517.18): C;30.19, H;1.56 F;62.45, N;2.71. Found: C;30.39, H;1.65, F;60.94, N;3.29.

Experiment 2

Block copolymer was produced by adding 21.8 mmoles of N-methyl-2-(2-perfluorooctyl)ethyloxazolinium tosylate to a solution of 88.8 mmoles of 2-(2-perfluorooctyl)ethyl-2-oxazoline in 200 mL of I,1,2,trichloroethane at 114° C., with stirring, and maintaining that temperature for 23 hr. After 23 hr. the temperature was reduced to 100° C., and 109 mmoles of 2-methyl-2-oxazoline was added. After 22 hr at 100°C., a 69% yield of polymer was isolated by precipitating into 2000 mL of ethyl ether, under N2. The molar ratio of 2-methyl-2-oxazoline to fluorinated oxazoline in the polymer was 1.79 (calculated from the ratio of carbon to fluorine as measured by elemental analysis), the number average molecular weight was 3820 and the weight average molecular weight was 7140, as measured by gel permeation chromatography.

EXAMPLE 1

Fibrinogen adsorption onto the tubes was performed within 12 hours of the preparation of the coated and uncoated tubing loops. Radiolabelled fibrinogen (I-125-fibrinogen) was added to cold or unlabelled fibrinogen solution with a protein concentration of about 10 microgram/mL. With freshly labelled fibrinogen (specific activity around 1.0 mCi/mL), this usually meant preparing a solution containing the following: 0.100 mL 125-I fibrinogen stock at 1.0 mg/mL, 0.025 mL unlabelled fibrinogen stock at 4.0 mg/mL and dilution to a final volume of 20 mL with 0.1 M sodium carbonate buffer, pH 9.6. The carbonate buffer was prepared by dissolving 1.59 g sodium carbonate, 2.93 g sodium bicarbonate and 0.2 g sodium azide in 1 liter volume of water. The amount of the radiolabelled fibrinogen added was such that the cpm would average between $0.90 \times 10^5 - 1.4 \times 10^5$ cpm per microgram of protein or per 0.100 mL of the working labelled fibrinogen solution. The washing buffer was drained from the coated or uncoated tubing loops and the radiolabelled fibrinogen solution was added. After air bubbles were cleared from the system, the loop was closed and the solution was circulated at 100 mL/min for 2 hours at room temperature. At the conclusion of the experiment, the radiolabelled protein solution was drained from the loop, a "dummy" or clean piece of Silastic ® tubing (approx. 7.5 cm) was connected to one end of the tubing loop and was inserted into a beaker containing approximately 200 mL washing buffer. The washing buffer consisted of PBS and 0.05% Tween 20. This solution was recirculated through the open loop for 2 hours. The loop was then disengaged and each polymer tubing sample was cut into 5 pieces of 1 cm length. Each 1 cm section was placed into a plastic test tube and counted in a gamma counter for 1 minute. The counts per minute (cpm) were averaged for the five replicate sections and the mean was compared against the labelled fibrinogen standard solutions. These standards were prepared by serial dilutions of the working labelled fibrinogen solution described above, with carbonate buffer to create solutions with fibrinogen concentrations ranging from 1 ng to $1 \times 10^4$ ng/mL. One mL of each standard protein solution was placed in a test tube and counted along with the other polymer tubing samples. The recorded cpm for these standard solutions comprise the standard calibration series against which the averaged counts for each of the polymer tubing samples were compared. Adsorbed fibrinogen amounts are shown below.

| Expt # | Uncoated (ng/cm$^2$) | Coated |
|---|---|---|
| 1 | 213 +/− 3.3 | 44.4 +/− 2.1 |
| 2 | 213 +/− 3.3 | 117 +/− 5.2 |
| 3 | 41.4 +/− 1.8 | 24.4 +/− 2.0 |

EXAMPLE 2

Canine Ex-vivo shunt with copolymer-coated and uncoated tubing.

The ex-vivo experimental model is useful for rapid characterization of the blood response to material surfaces. The tubing loop is exposed to blood streaming directly from the canine femoral artery and is recirculated back into the canine through the femoral vein. Synthetic polymer tubing loops were prepared as described above. These Teflon ® connectors were refluxed in 2% TDMAC-heparin solution for 30 minutes then allowed to air dry on the day of the shunt experiment. Beveled polyethylene catheters (sold by Intramedics) were attached to both ends of the tubing loops. A non-continuous shunt method was employed which exposed the tubing loop to a single time interval and the allowed SEM characterization of the surface after the shunt experiment. The animals were induced with thiopental sodium and maintained on halothane. The femoral artery and vein were isolated and two loose ligatures were placed proximal to the point of entry of the cannula on both vessels. Both vessels were ligated distal to the beveled catheter entry point. Vessels were clamped proximal to the loose ligatures and the catheters were fed into each vessel; the ligatures were tightened and the clamps were released. The catheter was fed into the vessel further and the ligatures were secured. The shunt circuit was then opened to full arterial blood flow (about 175 cc/min). The loop was exposed to the blood for 32 min, at which time the blood flow stopped due to an occlusion in the shunt. Immediately after the shunt was removed from the blood vessels, it was flushed with saline. Sections of the sample were placed in fixative solution (2% glutaraldehyde, 0.1 M cacodylate, pH 7.4) for 24 hours before transfer into phosphate buffered saline for scanning electron microscopy analyses. Animal care, post-surgery: Closure of the nicked vessel: the vessels were repaired with polypropylene sutures. The wound was then closed in three layers with 3-0 chromic gut suture: (a) medial femoral fascia was joined to the sheath of sartorius muscle; (b) subcutaneous tissue closure; and (c) skin closure. An antibiotic (Biocin, 1 mL) was administered prior to removal of the animal from anesthesia and was administered daily for one week post-surgery.

Scanning electron analysis: The sample sections remained wet in the PBS buffer until subjected to the dehydration sequence. The samples were dehydrated by sequential immersion in ethanol/water solutions at 70%, 85%, 95% and 100% ethanol concentrations, then hexamethyldisilazane for ten minutes. The samples were then dried at room temperature overnight. The samples were then mounted with carbon paint on aluminum stubs and coated with approximately 200 angstroms of gold in a Denton Sputter-coater. Samples were analyzed at various magnifications with an AMRAY scanning electron microscope. The cellular profile on the copolymer-coated polymer tubing surfaces is given below.

| MATERIAL | Cellular Profile |
|---|---|
| Polyurethane (uncoated) | activating platelets; small platelet aggregates |
| Polyurethane (coated) | occasional spreading white cells |

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A process for manufacturing a polyurethane part, comprising, contacting a polyurethane surface with an aqueous solution of a water soluble block copolymer of the structure

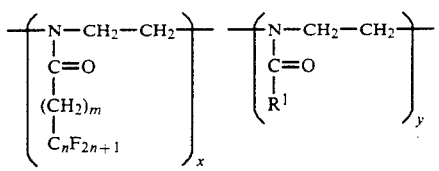

wherein:
m is 0, 1 or 2
n is an integer of 4 to about 16;
x is an integer of 3 to 100;
y is large enough so that the polymer is water soluble; and
$R^1$ is methyl or ethyl.

2. The process as recited in claim 1 wherein said polyurethane is flexible.

3. The process as recited in claim 1 wherein said polyurethane is made from a polyether polyol.

4. The process as recited in claim 3 wherein said polyol is poly(tetramethylene ether) glycol.

5. The process as recited in claim 1 wherein said polyurethane is made from one or more diamines containing 2 to 6 carbon atoms.

6. The process as recited in claim 5 wherein said amines are a combination of ethylenediamine and cyclohexanediamine.

7. The process as recited in claim 1 wherein said polyurethane is made from the isocyanate bis(4-isocyanatophenyl)methane.

8. The process as recited in claim 5 wherein said polyurethane is made from the polyol poly(tetramethylene ether) glycol, and from the isocyanate bis(4-isocyanatophenyl)methane.

9. The process as recited in claim 1 wherein said n is an integer of 6 to 12.

10. The process as recited in claim 9 wherein said n is 8.

11. The process as recited in claim 1 wherein said $R^1$ is methyl.

12. The process as recited in claim 1 wherein said x is 4 to 8.

13. The process as recited in claim 1 wherein said x is 5, said y is 9, said m is 2, and said n is 8.

14. The process as recited in claim 9 wherein said x is 5, said y is 9, said m is 2, and said n is 8.

15. The process as recited in claim 1 wherein the concentration of said block copolymer is about 0.1 to about 20 weight percent.

16. The process as recited in claim 15 wherein the concentration of said block copolymer is about 0.5 to about 5 weight percent.

17. The process as recited in claim 14 wherein the concentration of said block copolymer is about 0.5 to about 5 weight percent.

18. An article, comprising, a polyurethane part whose surface has been modified by contact with a block copolymer of the formula

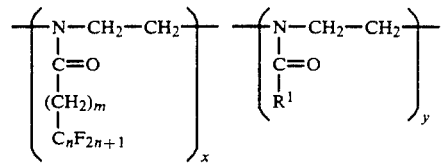

wherein:
m is 0, 1 or 2;
n is an integer of 4 to about 14;
x is an integer of 3 to 100;
y is large enough so that the polymer is water soluble; and
$R^1$ is methyl or ethyl.

19. The article as recited in claim 18 wherein said polyurethane is flexible.

20. The article as recited in claim 18 wherein said polyurethane is made from a polyether polyol.

21. The article as recited in claim 20 wherein said polyol is poly(tetramethylene ether) glycol.

22. The article as recited in claim 18 wherein said polyurethane is made from one or more diamines containing 2 to 6 carbon atoms.

23. The article as recited in claim 22 wherein said amines are a combination of ethylene diamine and cyclohexanediamine.

24. The article as recited in claim 18 wherein said polyurethane is made from the isocyanate bis(4-isocyanatophenyl)methane.

25. The article as recited in claim 22 wherein said polyurethane is made from the polyol poly(tetramethylene ether) glycol, and from the isocyanate bis(4-isocyanatophenyl)methane.

26. The article as recited in claim 18 wherein said n is an integer of 6 to 12.

27. The article as recited in claim 26 wherein said n is 8.

28. The article as recited in claim 18 wherein said $R^1$ is methyl.

29. The article as recited in claim 18 wherein said x is 4 to 8.

30. The article as recited in claim 18 wherein said x is 5, said y is 9, said m is 2, and said n is 8.

31. The article as recited in claim 26 wherein said x is 5, said y is 9, said m is 2, and said n is 8.

32. The article as recited in claim 18 wherein said m is 2.

33. The process as recited in claim 1 wherein said m is 2.

* * * * *